(12) United States Patent
Sutton

(10) Patent No.: US 6,505,080 B1
(45) Date of Patent: Jan. 7, 2003

(54) METHOD AND APPARATUS FOR INHIBITING OR MINIMIZING CALCIFICATION OF AORTIC VALVES

(75) Inventor: Richard Sutton, London (GB)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/558,869

(22) Filed: Apr. 28, 2000

(30) Foreign Application Priority Data

May 4, 1999 (GB) .............................. 9910301

(51) Int. Cl.$^7$ ................................ A61N 1/08
(52) U.S. Cl. ......................................... 607/72
(58) Field of Search ................... 600/374, 509; 607/4, 5, 7, 9, 62, 67, 72, 74, 119

(56) References Cited

U.S. PATENT DOCUMENTS 5,755,761 A * 5/1998 Obino .................. 607/122
6,047,700 A * 4/2000 Eggers et al. ........... 128/898

* cited by examiner

Primary Examiner—George R. Evanisko
Assistant Examiner—Frances P. Oropeza
(74) Attorney, Agent, or Firm—Thomas F. Woods; Eric R. Waldkoetter; Tom G. Berry

(57) ABSTRACT

The invention relates to a method and apparatus for minimizing calcification of a heart valve wherein electric energy is supplied to the heart in the region of the aortic valve during the refractory period of the heart.

4 Claims, 4 Drawing Sheets

METHOD AND APPARATUS FOR INHIBITING OR MINIMIZING CALCIFICATION OF AORTIC VALVES

FIELD OF THE INVENTION

The present invention relates to a method and apparatus for minimizing calcification of a heart valve.

BACKGROUND OF THE INVENTION

The build up of calcified deposits on the superior surface of the aortic heart valve accounts for a large number of aortic stenosis cases. This condition is characterised by the build up of calcified nodules on the upper and superior surface of the valve leaflets. These nodules decrease the flexibility of the leaflets, thereby limiting their mobility and capacity to fully open to permit adequate blood flow.

One technique to correct aortic stenosis is valve replacement.

Heart valve replacement operations have been carried out for several years, on patients having degenerating heart valves.

A number of types of replacement heart valves are known, including porcine and non-porcine artificial valves.

Replacement heart valves made from treated tissue, such as pig valves, may also become less flexible and lose their effectiveness due to calcification, i.e. the build-up of calcified deposits on the surface of the aortic heart valves. This build up again limits the mobility of the valve leaflets and their capacity to fully open to permit adequate blood flow.

Accordingly, it is important to monitor the condition of implanted artificial heart valves. Early calcification can be a life-threatening complication which must be recognised promptly and treated by emergency valve replacement.

Furthermore, in some patients, valve replacement is not a viable option. For valve replacement to be possible, the patient must be healthy enough to undergo open heart surgery. Further, a patient receiving a replacement valve typically must take anticoagulation drugs for the rest of his or her life. Also, some patients have an aortic root that is not large enough to easily accommodate conventional replacement valves. For such patients, it is also important to monitor the aortic valve which may be susceptible to the build up of calcified deposits and to minimise the calcification, where possible.

U.S. Pat. No. 4,769,032 by Steinberg teaches a prosthetic valve and monitoring system which replaces the need for an echocardiogram by allowing the recipient to monitor his own valve continuously at home, or periodically in a Doctor's office or a clinic etc. An artificial heart valve is provided with means for generating a detectable electrical current upon motion of the valve leaflets responsive to blood flow therethrough. The current signal can then be analysed to determine the condition of the leaflet. The leaflets of the artificial heart valve may be impregnated with magnetizing ions prior to implantation of the valve into the heart. Thereafter, blood flow through the heart valve opens the ion-impregnated heart leaflets. The motion of the leaflets induces a voltage in a solenoid coil opposed to the valve. The voltage varies in accordance with the velocity at which the valve leaflets open.

Many methods of treating artificial valves prior to implantation, to inhibit calcification after implantation, are known. Examples of such methods are disclosed, for example, in U.S. Pat. No. 5,051,401; U.S. Pat. No. 4,323,358; U.S. Pat. No. 4,378,224; U.S. Pat. No. 4,553,974; U.S. Pat. No. 4,648,881 and U.S. Pat. No. 5,002,566. In the latter of these, calcification-resistant bioprosthectic implants are made from tanned biological materials, e.g. porcine heart valves, bovine pericardium, human dura mater, etc which has been impregnated with a calcification-mitigating effective amount of a ferric and/or stannic salt. The impregnated biological materials and processes are particularly advantageous for the preparation of bioprosthetic heart valves. These implants have been planned to be highly resistant to calcification, in vivo.

It would be desirable to provide a system for treating a valve, particularly an artificial valve after implantation, in vivo.

U.S. Pat. No. 5,443,446 teaches a method and apparatus for in vivo heart valve decalcification. The apparatus for mechanical in vivo removal of calcified deposits from the valve includes an anchoring balloon catheter fixable across the valve, a tool for removing the deposit, and a mechanism for securing the tool with respect to the anchoring balloon and the aortic valve. A number of position balloons can be selectively inflated and deflated to correctly position the deposit removal tool.

The above US patent, however, does not act to prevent or minimize the build up of calcium deposits in the first place, but merely removes calcified deposits which have built up.

According to the present invention, there is provided a method and apparatus for minimizing or inhibiting the build up of calcified deposits on an aortic valve, in vivo.

According to a first aspect, there is provided a method of inhibiting build-up of calcified deposits on an aortic valve, comprising applying electrical energy to the heart in the region of the valve, during the refractory period of the heart.

According to a second aspect, there is provided an implantable apparatus for inhibiting the build-up of calcified deposits on an aortic valve comprising an implantable pulse generator; means for sensing depolarizations of the heart; means for applying electric energy generated by the implantable pulse generator, to the heart, and control means for controlling the delivery of the electric energy to the heart in dependance on the detected depolarizations; wherein said control means is adapted to cause electrical energy to be applied to the heart in the region of the aortic valve during refractory periods of the heart.

SUMMARY OF THE INVENTION

The present invention provides a method and apparatus for preventing, or at least mitigating the build up of calcium on the tissue valve by treating the tissue valve within the body, i.e. in vivo, with electrical signals. In particular, in the preferred embodiment, the present invention uses a bipolar electrode in the high right atrium to "focus" the electrical current onto the tissue valve during the ventricular refractory period.

BRIEF DESCRIPTION OF THE DRAWINGS

The present invention will now be described, by way of example only, with reference to the accompanying drawings.

DETAILED DESCRIPTION OF THE DRAWINGS

Figure 1A:
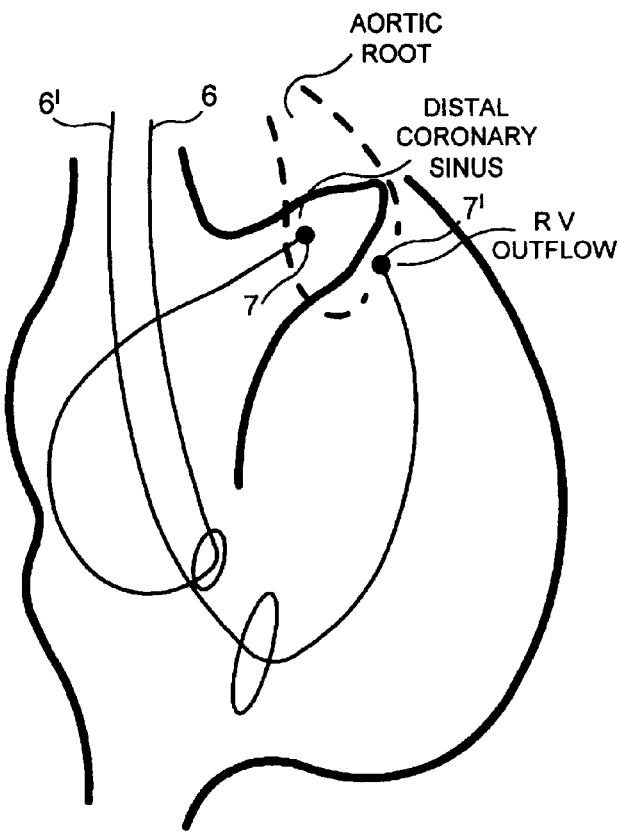
FIGS. 1A and 1B show a patient's heart having an implanted aortic valve and apparatus according to the present invention implanted in the heart.
Figure 1B:
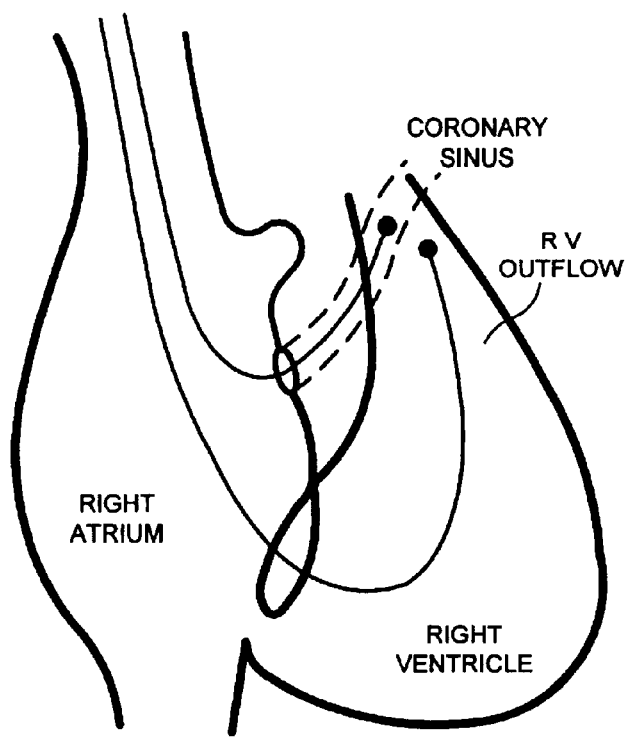

Referring to FIGS. 1A and 1B, there are shown diagrams of a patient's heart 1 having an implanted artificial aortic valve 2, and an implantable pacemaker 3 adapted to provide electrical energy to minimise or inhibit calcification of the valve 2.

The pacemaker 3 is provided with a hermetically sealed enclosure 4, typically fabricated of a biocompatible metal such as titanium. Mounted to the top of the enclosure 4 is a connector block 5 which receives electrical connectors located on the proximal ends of leads 6, 6'. Leads 6, 6' each carry two electrodes 7, 7' and 8, 8'. Electrodes 7 and 8 are used both to sense atrial depolarizations and to deliver electrical energy to the site near the implanted valve 2. Electrical energy may be delivered between electrode 7 and 8 or between electrode 8 and the housing of the pacemaker. Sensing of atrial depolarizations may occur between electrodes 7 and 8 or between either of the electrodes and the housing of the pacemaker.

Electrodes 7' and 8' are used to sense ventricular depolarizations.

Figure 2:
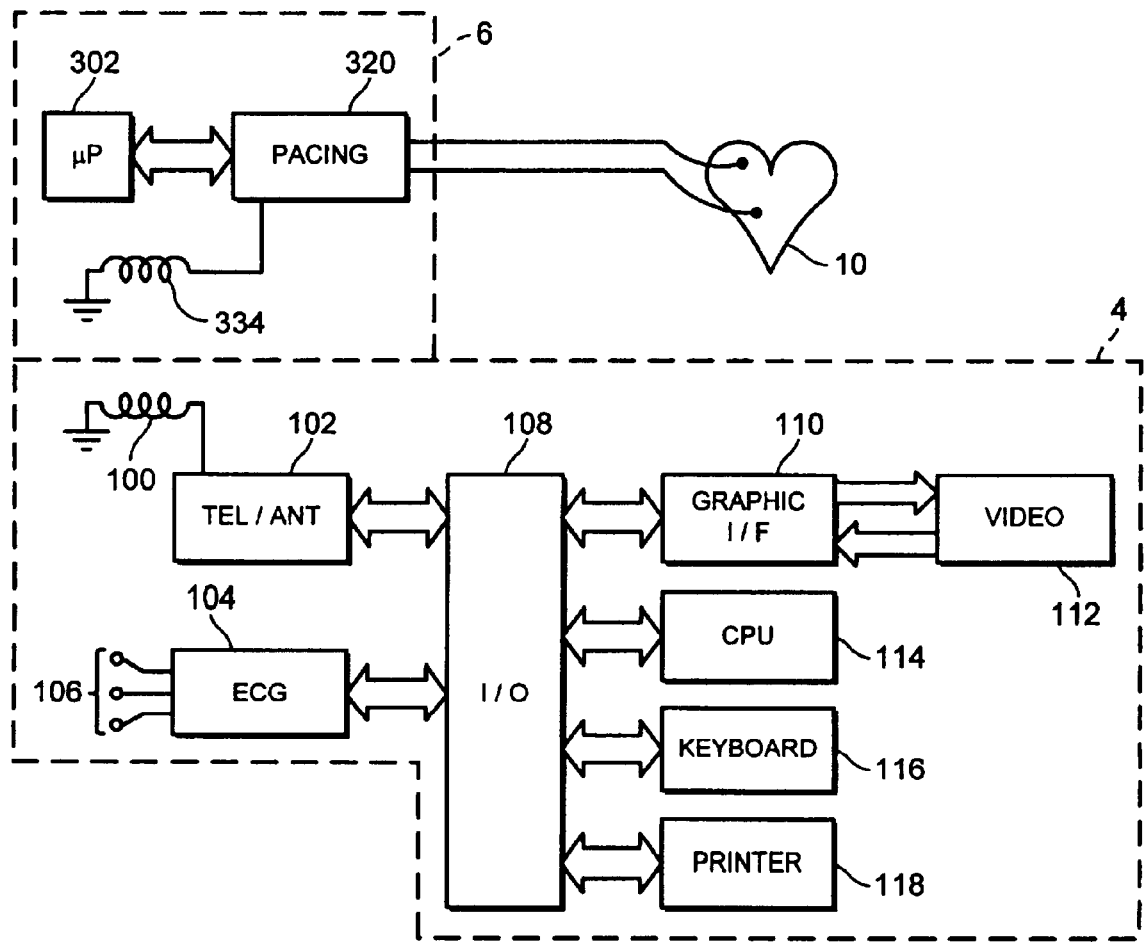
FIG. 2 is a block diagram of an implantable pacemaker capable of carrying out the method of the invention.

FIG. 2 illustrates the pacemaker in block diagram form, coupled to the heart 1, in conjunction with an external programmer/display apparatus corresponding to those typically employed to program modern, multi-programmable implantable pacemakers.

Within the pacemaker housing are located the pacing circuitry 320, which includes circuitry performing all of the basic timing, stimulation and sensing functions of a cardiac pacemaker and a microprocessor circuit 302 which controls the timing intervals provided by the pacing circuitry 320.

Pacing circuitry 320 also includes a bidirectional telemetry circuit coupled to an antenna 334, allowing transmission of information from an external programmer into the pacemaker to modify its parameters and allow transmission of information from the pacemaker to the external programmer, again generally corresponding to telemetry and programming systems presently existing in commercially marketed multi-programmable implantable pacemakers.

The external programmer also includes a corresponding antenna 100 coupled to a telemetry/antenna driver circuit 102 which serves to demodulate telemetry signals received from antenna 334 of the pacemaker, and to apply them in parallel or serial digital format to input/output (I/O) unit 108, where they in turn may be applied to a video monitor 112 via graphic interface 110, and/or provided to a central processing unit 114 and/or printer 118.

Microprocessor 114 controls the operation of the programmer/ display apparatus, and is responsive to physician entered commands via keyboard 116, for controlling programming signals sent to the pacemaker, as well as for controlling operation of the video display 112 and printer 118.

Also illustrated is an ECG interface 104, coupled to three ECG electrodes 106 intended to be placed on the patient's body. ECG interface 104 provides sensed electrograms to input/output device 108, where they in turn may be provided to the video display 112, the central processing unit 114 or the printer 118.

The digital controller/timer circuit 330 is programmed to define an atrial refractory period during which the electrical energy is to be provided to the electrode 7 located in the high right atrium, close to the valve. The effect of applying energy close to the valve is to inhibit calcification as described above.

Figure 3:
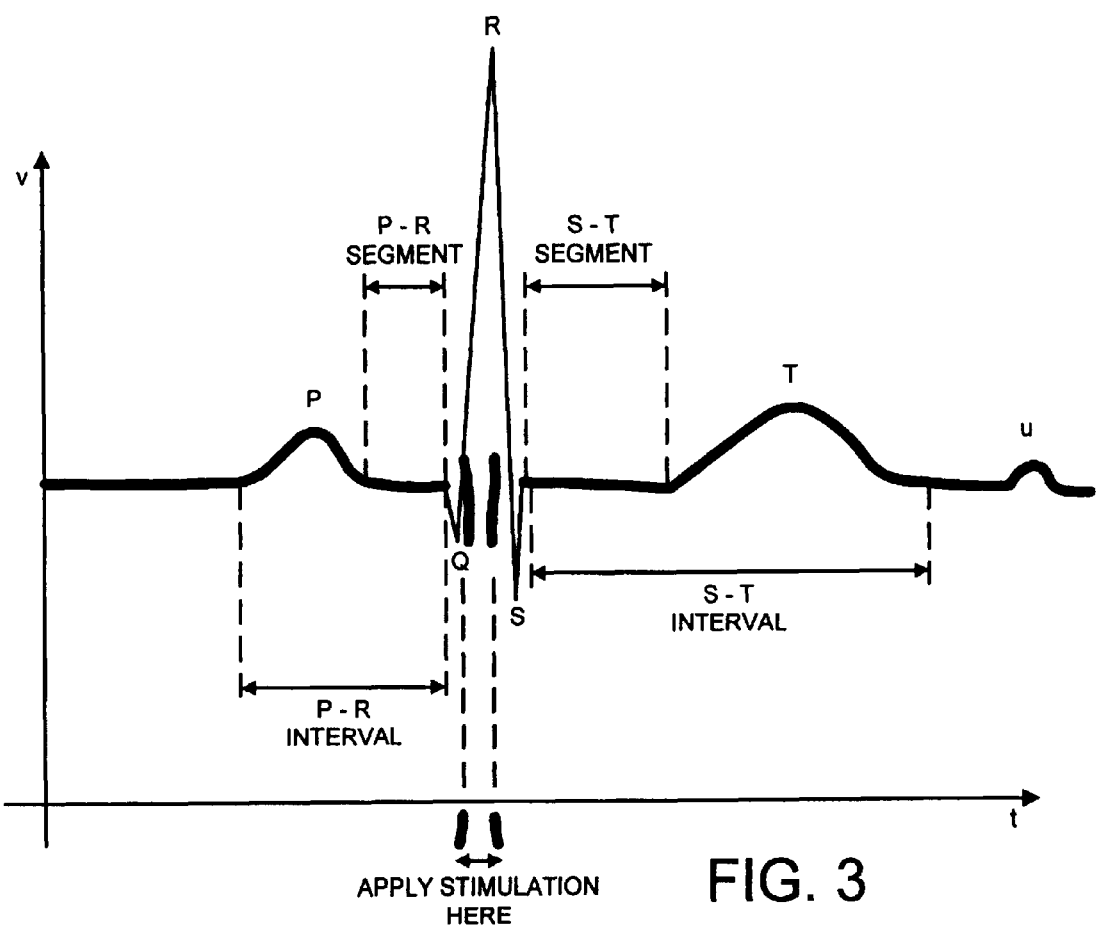
FIG. 3 is a timing diagram illustrating to operation of the apparatus of FIG. 1.

FIG. 3 is a timing diagram showing the timing of application of the calcification inhibiting pulses, in relation to the cardiac activity of the patient. Preferably, stimulation is applied within the R-wave.

The pulse parameters may be selected on a case by case basis, taking into account a wide range of factors. The physician may also select the duration and/or time of day of application of stimulation. For example, in some cases stimulation may be applied throughout the day. In other cases stimulation may be applied only at night or when the patient is at rest. Stimulation should preferably not exceed 150 ms, so as not to cause fibrillation.

In one embodiment, the apparatus is a 'smart' device having means for detecting the actual degree of calcification and means for adjusting the pulse parameters or otherwise controlling the stimulation accordingly.

Figure 4:
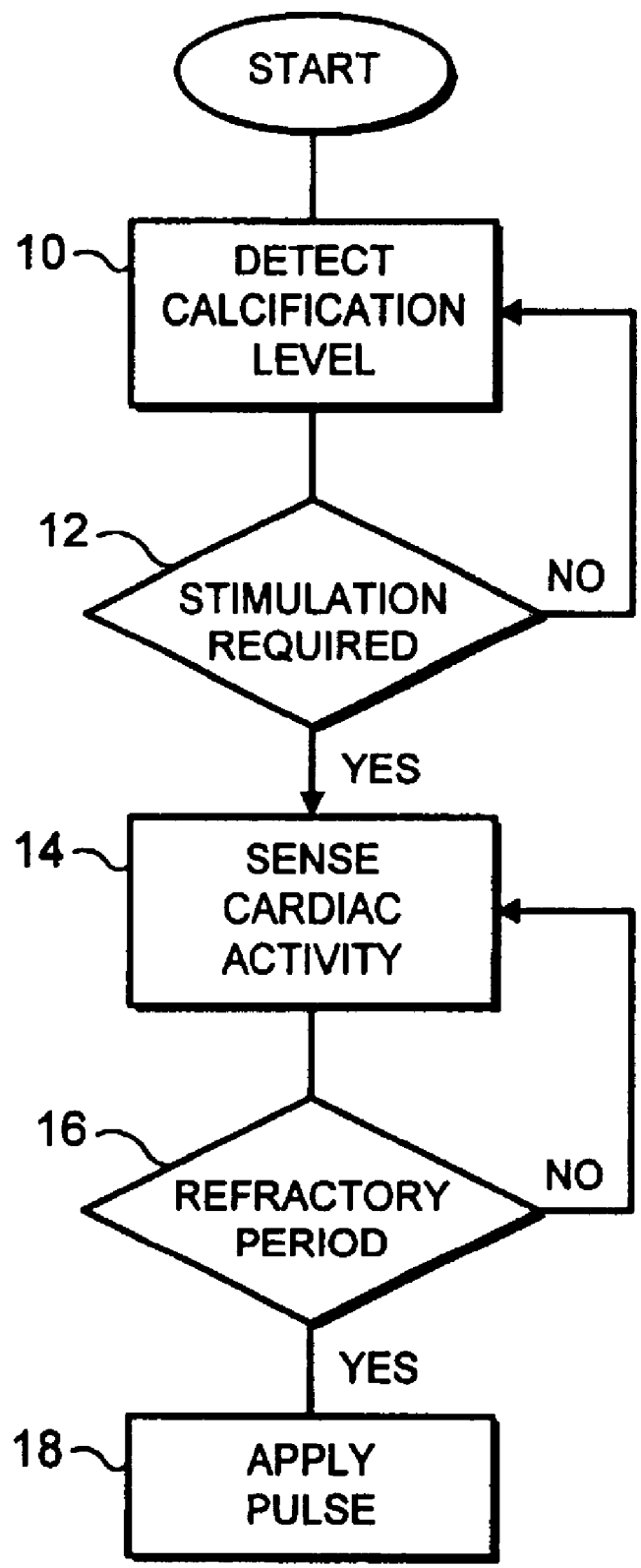
FIG. 4 shows a flow chart illustrating the steps of a method according to the present invention.

FIG. 4 shows the steps involved in this embodiment. In step 10, the level of calcification is detected. This level is compared to a threshold level to determine if stimulation is required (step 12). If it is determined that stimulation is necessary to inhibit calcification, the cardiac activity of the patient is monitored (step 14). When the defined refractory period is detected (step 16) the pulse of electrical energy is applied (step 15).

What is claimed is:

1. An implantable apparatus for in vivo inhibition of the build-up of calcified deposits on an aortic valve of a human subject, the apparatus comprising:
    an implantable pulse generator;
    a first implantable medical electrical lead for sensing depolarizations of a heart, the first lead being operably connected to the pulse generator and being configured for placement in a right ventricular outflow of the heart, the first lead further comprising at least a first electrode located at or near a distal end of the first lead;
    a second implantable medical electrical lead for sensing depolarizations of the heart and applying electrical stimuli to a site near an artificial aortic valve implanted in an aorta of the heart, the second lead being operably connected to the pulse generator and being configured for placement in a coronary sinus of the heart, the second lead further comprising at least a second electrode located at or near a distal end of the first lead, and
    a controller, located in the pulse generator and operably connected to the first and second leads and the first and second electrodes, for sensing depolarizations detected by the first or second leads and for controlling the delivery of the electrical stimuli to the heart in dependence on the detected depolarizations;
    wherein said controller is adapted to cause the electrical stimuli to be applied to the heart in the region of the aortic valve through the second lead during refractory periods of the heart.

2. The apparatus of claim 1, wherein said second lead further comprises a third electrode for permitting the second lead to apply electrical stimuli between the second and third electrodes.

3. The apparatus of claim 1, wherein said controller comprises a microprocessor.

4. The apparatus of claim 1, further comprising a telemetry system for exchanging information between the implantable device and an external device.

* * * * *